US006509148B2

(12) United States Patent
Cha et al.

(10) Patent No.: US 6,509,148 B2
(45) Date of Patent: *Jan. 21, 2003

(54) METHOD FOR FABRICATING BIOSENSORS USING HYDROPHILIC POLYURETHANE

(75) Inventors: Geun Sig Cha, Seoul (KR); Hakhyun Nam, Seoul (KR); Jae Ho Shin, Seoul (KR)

(73) Assignee: i-Sens, Inc., Seoul (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,513

(22) PCT Filed: Jul. 9, 1999

(86) PCT No.: PCT/KR99/00368
§ 371 (c)(1),
(2), (4) Date: Feb. 10, 2000

(87) PCT Pub. No.: WO00/03222
PCT Pub. Date: Jan. 20, 2000

(65) Prior Publication Data
US 2002/0107227 A1 Aug. 8, 2002

(30) Foreign Application Priority Data
Jul. 9, 1998 (KR) .............................................. 98-27563

(51) Int. Cl.[7] .......................... C12Q 1/00; G01N 33/53; G01N 33/543; G01N 33/00; G01N 27/26; C08F 2/46

(52) U.S. Cl. ...................... 435/4; 435/7.1; 435/7.4; 435/7.92; 435/177; 435/180; 435/181; 435/287.2; 435/287.9; 436/85; 436/518; 436/528; 436/531; 436/532; 422/68.1; 422/76; 422/82.01; 422/82.02; 422/82.03; 422/82.11; 422/83; 422/90; 522/1; 324/714; 204/196.06; 204/400; 204/403; 204/410; 204/415; 204/416; 204/418; 204/421; 204/422; 204/424; 204/426; 204/428; 204/429; 204/431

(58) Field of Search .................... 204/196.06, 400, 204/403, 410, 415, 416, 418, 421, 422, 424, 426, 428, 429, 431; 324/714; 422/68.1, 76, 82.01, 82.02, 82.03, 82.11, 83, 90; 435/7.1, 7.4, 4, 7.92, 177, 180, 181, 287.2, 287.9; 436/85, 518, 528, 531, 532; 522/1

(56) References Cited

U.S. PATENT DOCUMENTS

| | | | | |
|---|---|---|---|---|
| 4,312,946 A | * | 1/1982 | Wood et al. | 435/180 |
| 4,454,007 A | * | 6/1984 | Pace | 204/1 T |
| 4,534,355 A | * | 8/1985 | Potter | 204/403.07 |
| 4,979,959 A | * | 12/1990 | Guire | 623/66 |
| 4,987,075 A | * | 1/1991 | Nentwig et al. | 435/182 |
| 5,042,144 A | * | 8/1991 | Shimada et al. | 29/825 |
| 5,096,671 A | * | 3/1992 | Kane et al. | 422/82.07 |
| 5,102,526 A | * | 4/1992 | Brown et al. | 204/415 |
| 5,264,104 A | * | 11/1993 | Gregg et al. | 204/403 |
| 5,334,691 A | * | 8/1994 | Gould et al. | 424/409 |
| 5,403,750 A | * | 4/1995 | Braatz et al. | 436/531 |
| 5,415,746 A | * | 5/1995 | Cha | 204/153.12 |
| 5,540,828 A | * | 7/1996 | Yacynych | 204/418 |
| 5,611,900 A | * | 3/1997 | Worden et al. | 204/403 |
| 5,863,972 A | * | 1/1999 | Beckelmann et al. | 524/186 |
| 5,897,955 A | * | 4/1999 | Drumheller | 428/422 |
| 5,998,200 A | * | 12/1999 | Bonaventura et al. | 106/15.05 |
| 6,106,505 A | * | 8/2000 | Modak et al. | 424/422 |
| 6,214,185 B1 | * | 4/2001 | Offenbacher et al. | 204/403 |
| 6,238,930 B1 | * | 5/2001 | Spichiger-Keller et al. | 436/518 |
| 6,241,863 B1 | * | 6/2001 | Monbouquette | 204/403 |

FOREIGN PATENT DOCUMENTS

| | | |
|---|---|---|
| WO | WO-91/17432 A1 | * 11/1991 |
| WO | WO9204438 | 3/1992 |
| WO | WO9630431 | 10/1996 |

OTHER PUBLICATIONS

Liu et al. Potentiometric ion– and bioselective electrodes based on asymmetric polyurethane membranes. Analytica Chimica Acta vol. 274, No. 1 (1993) pp. 37–46.*

Shin et al. Potentiometric biosensors using immobilized enzyme layers mixed with hydrophilic polyurethane. Sens. Actuators vol. B50, No. 1 (1998) pp. 19–26.*

* cited by examiner

*Primary Examiner*—Long V. Le
*Assistant Examiner*—Kartic Padmanabhan
(74) *Attorney, Agent, or Firm*—Bachman & LaPointe, P.C.

(57) ABSTRACT

Disclosed is a method for fabricating biosensors, using hydrophilic polyurethane. Bio-active reagents, including enzymes, antibodies, antigens, cells and receptors, are mixed with hydrophilic polyurethane and the mixture is directly coated over a signal transducer to form a sensing film which serves as a signal detector. The method using hydrophilic polyurethane allows the simplification of the fabrication of biosensors without conducting complicated chemical reactions and washing steps, such as crosslinking. The bio-active reagent entrapped within the hydrophilic polyurethane film can retains its high activity for an extended period of time and the intrinsic potentiometric response of the underlying ion-selective polymeric membrane is not affected by the bio-active reagent immobilized polyurethane film coated on its sensing surface. Therefore, the biosensors are superior in specificity, selectivity, and stability. Also, the adoption of solid-state type electrodes by virtue of the direct immobilization of the bio-active reagents allows the biosensors to be miniaturized, offering the advantages of the detection of small quantities of samples and mass production for low cost.

14 Claims, 9 Drawing Sheets

METHOD FOR FABRICATING BIOSENSORS USING HYDROPHILIC POLYURETHANE

This is the U.S. National Stage Application of PCT/KR99/00368 filed on Jul. 7, 1999.

BACKGROUND OF THE INVENTION

1. Field of the Invention

The present invention relates to a method for fabricating a biosensor composed of a signal detector and a signal transducer. More particularly, the present invention relates to the direct immobilization of the signal detector on the signal transducer by use of hydrophilic polyurethane, thereby fabricating a biosensor which is superior in specificity, selectivity, and stability.

2. Description of the Prior Art

Targeting biochemical materials as analytes or as leads during signal generation, biosensors, like typical chemical sensors, consist mainly of signal detectors and signal transducers. In the signal detectors, bio-active reagents such as enzymes, antibodies, receptors, cells, etc., react with recognizable biochemical objects such as substrates, antigens, ligands, cells, etc., to cause physical and/or chemical signals which are quantitated in the signal transducers with the aid of physical or chemical measuring apparatus. For converting the physical or chemical signals into measurable ones, there may be taken an optical technique in which optical density, fluorescence or absorbance is measured, an electrochemical technique such as voltametry, potentiometry or conductometry, a calorimetric technique such as thermometry, or a mechanical change sensing technique such as a surface acoustic wave sensing method. Of them, electrochemical biosensors are now known to be suitable for the rapid and accurate determination of various metabolites, including urea, glucose, cholesterol, lactate, creatinine, amino acids, etc. Particularly, since the late 1970s in which glucose biosensors were developed to diagnose diabetes at home, biosensors have been applied for a wide range of fields; e.g., medical and diagnostic fields for drug detection, food and sanitary fields, environmental fields, and manufacturing process fields.

The most important factors for the analysis of biosensors include the specificity and the sensitivity for the targets to be analyzed. While the specificity for targets is dependent on the biochemical properties of the bio active reagents, the sensitivity is determined by the recognition efficiency of sensing elements and the performance of signal detection and signal transduction in the biosensors fabricated. Biosensors enjoy a characteristic advantage, different from those which chemical sensors have, of showing excellent specificity for targets as well as maintaining high sensitivity by virtue of the molecular recognition of the bio active reagents.

However, biosensors also suffer from a disadvantage in that it is very difficult to obtain highly reliable and accurate analysis results because the targets exist at trace amounts with great difference in biochemical properties and molecular weights and the signals are generated through complex reaction pathways. In order to maximize the sensitivity of biosensors with efficiency in the detection of analytes, the bio-active reagents are preferably immobilized in a layer adjacent to the sensing surface of the basic electrochemical transducer. More preferably, the bio-active reagents are immobilized in such a way to react with their targets at maximal magnitudes. Another requirement is that the bio-active reagents should maintain their entities without reduction or extinction of their biochemical activity. Therefore, the immobilization of the bio-active reagents, such as enzymes or functional proteins, on an appropriate support occupies an important position in the research on biosensors. In addition, active research has been directed to the introduction of the biosensors into solid-state electrodes because they can offer the advantage of miniaturization, and mass fabrication for cost reduction.

To approach the immobilization of the bio-active reagents, chemical techniques, physical techniques or combinations thereof are usually used. First, as for the physical techniques, they are representatively exemplified by the adsorption of the bio-active reagents in water-immiscible carriers and the entrapment of the bio-active reagents in water-immiscible polymer gels. The chemical immobilization is accomplished via, for example, covalent bonds or crosslinks.

In the adsorption method, which is the oldest in immobilizing the bio-active reagents in or on supports, advantage is taken of the hydrophilicity, hydrophobicity or ionic reciprocal reaction between the bio-active reagents, such as enzymes, antibodies, receptors, cells, etc., and the supports, such as membranes or films. The molecules immobilized through the adsorption are disadvantageous in that they are easily desorbed from the signal transducers.

Physically trapping the bio-active reagents in membranes or films, the entrapment method is routinely applied for where non-chemical treatments or mild reaction conditions are needed. This method is known to be most suitable for the labile bio-active materials which are liable to lose activity under a strong condition, but the bio-active reagents are loosely attached to the supports, so they are easily detached therefrom, thus decreasing the performance of the biosensors.

The covalent bonds through which the bio-active reagents are chemically immobilized on the surface of the signal transducers are typically achieved by the reaction with activated surface functional groups, such as peptide, thiol, amine and epoxy. The surface of the biosensors thus fabricated is stable to pH, ionic strength and temperature change. However, there appears a problem in that the molecules immobilized by covalent bonds, especially enzymes or receptors, may be restricted in activity.

Taking advantage of both the entrapment method and the covalent bond method, the crosslinking immobilization method uses a crosslinking agent to form additional chemical bonds through which the bio-active reagents are immobilized in membranes or films. In this regard, glutaraldehyde or hexamethylene diisocyanate serves as a crosslinking agent.

The most prevailing immobilization method is to use glutaraldehyde to bond enzymes to poly(vinyl chloride) (PVC). This immobilization method, however, suffers from disadvantages in that poor bonds exist between the enzyme layer and the hydrophobic polymer, resulting in deteriorating the performance and life span of the biosensors.

Recently, to solve the above problems, there have been developed an asymmetrically modified polymeric ion selective membrane on the surface of which a thin layer of enzyme can be formed for use in biosensors. The asymmetric membrane is based on polyurethane and prepared by coating a thin hydrophilic polyurethane film on a polyurethane film containing plasticizers and ionophores or ion carriers. In such an asymmetric membrane, a bio-active reagent is introduced on the surface of the hydrophilic polyurethane by the crosslinking method. Upon using glutaraldehyde as a crosslinking agent, an amine group is usually selected to afford a host in which an enzyme is anchored through a covalent bond, so as to form a thin layer of enzyme. The amine group may be provided to the hydrophilic polyurethane film by preparing it from a mixture of polylysine and hydrophilic polyurethane. Because the enzyme layer thus formed is found to be superb in the bonding strength to the ion-selective membrane, this is readily available to fabricate solid-state type biosensors. However, many complicated reaction steps and washing procedures which must be taken in the fabrication course of the biosensors make it difficult to commercialize the crosslinking method.

SUMMARY OF THE INVENTION

As a consequence of the intensive and thorough research on biosensors, repeated by the present inventors, it was found that a biosensor prepared by directly incorporating a sensing material into a hydrophilic polyurethane membrane shows superb stability and an exceptionally extended life span and the complicated process steps, such as those needed in conventional crosslinking methods, can be significantly reduced.

Therefore, it is an object of the present invention to overcome the above problems encountered in prior arts and to provide a method for fabricating a biosensor, which allows the simplification of the fabrication of biosensors without conducting complicated chemical reactions.

In accordance with the present invention, the above object could be accomplished by a provision of a method for fabricating a biosensor composed of a signal detector and a signal transducer, in which the signal detector is formed by mixing a sensing material with hydrophilic polyurethane and directly immobilizing the mixture on the signal transducer.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

In the present invention, a sensing entity is mixed with hydrophilic polyurethane, so as to directly immobilize the signal detector in the signal transducer without conducting crosslinking reactions.

In detail, the direct immobilization of the present invention is conducted by mixing a solution of a bio-active reagent in a buffer with a solution of hydrophilic polyurethane in an organic solvent, coating the mixed solution on an electrode or membrane and drying it.

In an alternative embodiment, when the bio-active reagent is mixed with hydrophilic polyurethane, polylysine is added to enhance the permeability of the membrane. Being a constituent for the membrane, polylysine, highly hygroscopic, plays a role in controlling the hydrophilicity and porosity of the membrane.

As the bio-active reagent, enzymes, antibodies, cells or molecule receptors may be selected.

To provide appropriate hydrophilicity to the hydrophilic polyurethane, a controlled mole ratio between poly(ethylene glycol) (hereinafter referred to as "PEG") and poly (propylene glycol) (hereinafter referred to as "PPG") is used when preparing the polyurethane, ranging from 1:10 to 10:1 and preferably from 1:5 to 5:1.

From the group consisting of tetrahydrofuran (hereinafter referred to as "THF"), methanol and the mixture thereof is selected the organic solvent which can dissolve the hydrophilic polyurethane.

In quantitating the biochemical change caused by the bio-active reagent, the signal transducer of the biosensor prepared uses, for example, potentiometry, voltametry and/or conductometry. The base material of which the transducer is made is selected from the group consisting of silicon rubber, poly(vinyl chloride) and its derivatives, aromatic polyurethane, aliphatic polyurethane, and the mixtures thereof.

The targets at which the biosensors prepared according to the present invention aim, include various metabolites, such as urea, cholesterol, glucose, creatinine, adenosine, lactate and amino acids.

Figure 1A:
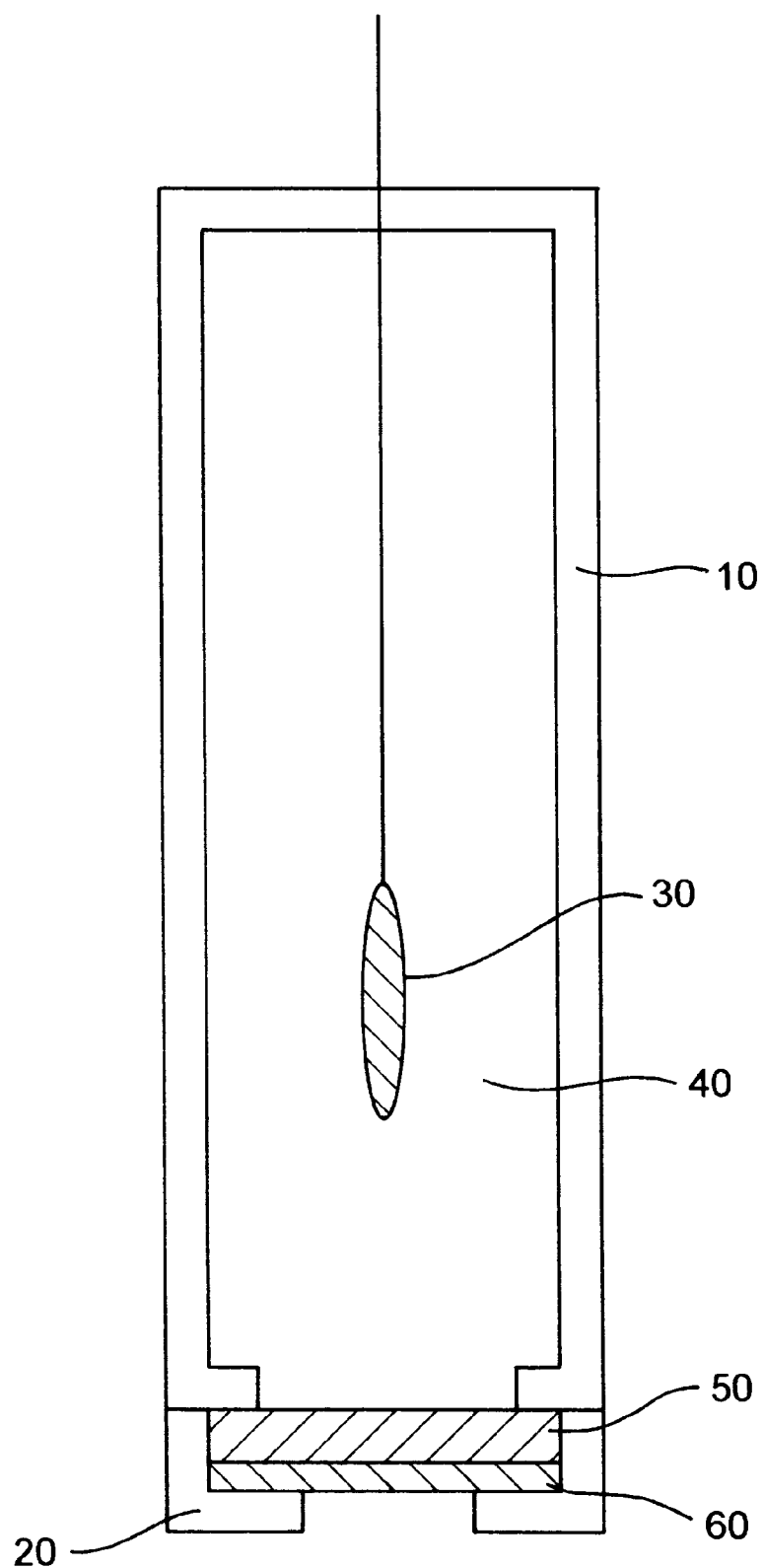
FIGS. 1a to 1c are schematic views showing a conventional type (1a), a wire type solid-state wire type (1b) and a planar type solid-state (1c) of biosensors.
Figure 1B:
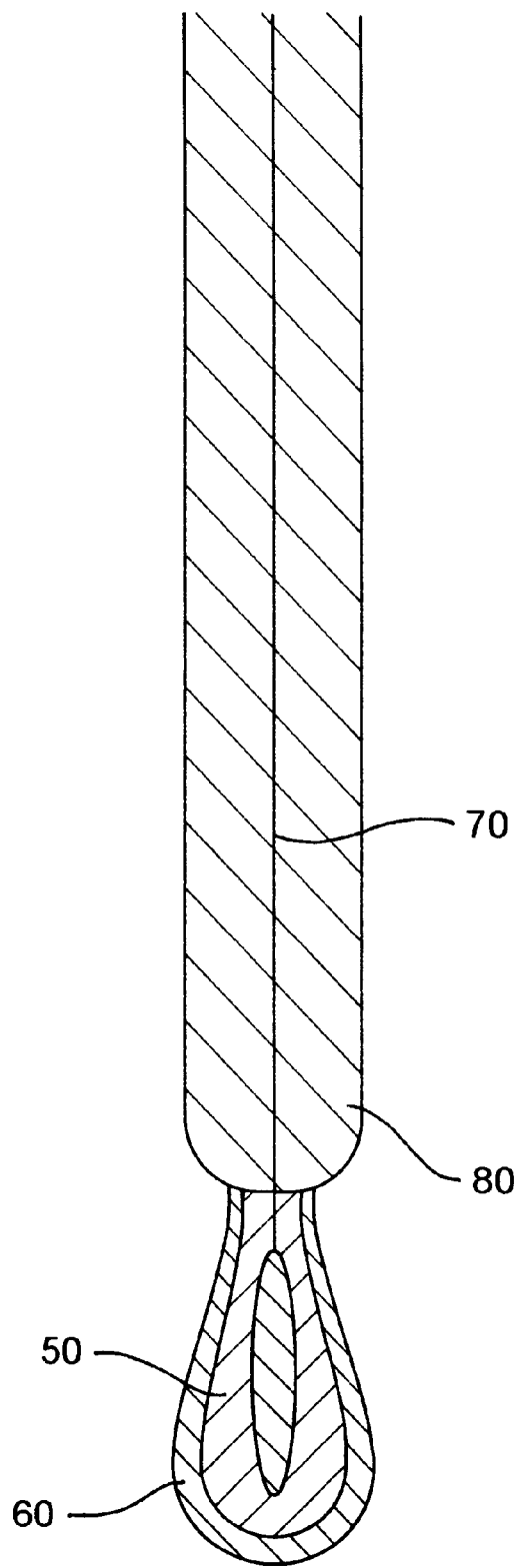
Figure 1C:
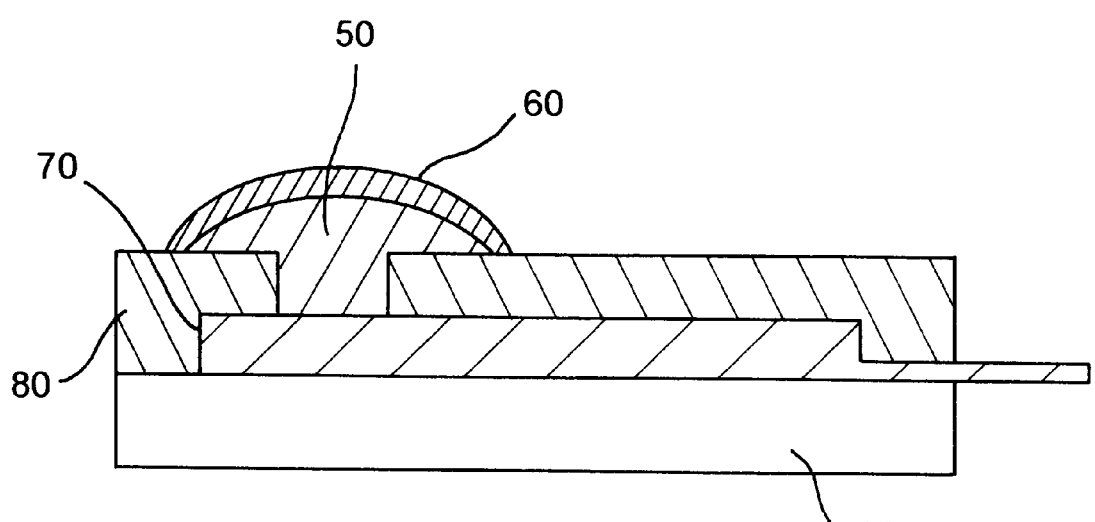

In accordance with the present invention, conventional electrodes or solid-state electrodes are employed to fabricate potentiometric biosensors. Referring to FIG. 1, there are shown a conventional electrode (1a) comprising a body of electrode 10, internal reference electrode 30, internal reference solution 40, a support part 20 which supports ion-selective membrane 50 on enzyme layer 60, a wire type solid state electrode (1b) wherein enzyme layer 60 surrounds selective membrane 50 and reference electrode 70 is surrounded in part by insulator 80 and a planar solid state electrode (1c)wherein the planar solid state electrode 9 has reference electrode 70 surrounded in part by insulator 80 with selective membrane 50 and enzyme layer 60, all of which are used in biosensors. As shown in the figures, the solid-state type biosensor can be prepared by the direct introduction of a polymeric membrane onto the surface of the electrode with no internal reference electrolyte solutions, in contrast to the conventional electrode-based biosensor. Therefore, the adoption of solid state type electrodes allows the biosensors to be miniaturized, offering the advantages of the detection of small quantities of samples and mass production for low cost.

Below, a detailed description will be given of the fabrication of a urea biosensor with application for an adenosine biosensor and a glucose biosensor, but is not set forth to limit the spirit and scope of the present invention.

To fabricate a biosensor for urea, a urease which catalyzes the hydrolysis of urea to produce carbon dioxide and ammonia is recruited as a sensing material. An enzyme layer is obtained through the direct immobilization of the present invention, in which the urease is mixed with hydrophilic polyurethanes synthesized with a variety of mole ratios between PEG and PPG, and coated over an electrode membrane.

Evaluation is made of the potentiometric response of the biosensors fabricated. The response and detection limit toward ammonium ions of the asymmetric electrode membranes in which the enzyme layers prepared from mixtures of hydrophilic polyurethanes and urease are introduced, are found to be similar to those of the electrode membrane lacking the enzyme layer, indicating that the presence of an additional hydrophilic polyurethane layer does not significantly affect the electrochemical properties of the underlying signal detecting polymeric membrane. Compared with the asymmetric electrode membranes in which urease are directly immobilized, on the other hand, a relatively slower response behavior is observed in an asymmetric electrode membrane in which a crosslinked enzyme film is formed over a hydrophilic polyurethane layer by the glutaraldehyde method, owing to the shielding effect of the constituting three layers: hydrophilic polyurethane layer, polylysine layer and enzyme film. For a similar reason, the electrode membrane comprising a crosslinked urease film is slower in the response toward urea than are the membranes employing directly immobilized urease. From the above observation, it should be noted that the electrode membranes which are used to introduce enzymes into the biosensors, exhibit similar response performance regardless of the type of the hydrophilic polyurethane used, indicating that they have no influence on the detection capability of the biosensors.

In order to investigate the influence of the shape of electrodes on the detection capability of the asymmetric urea biosensor in which an enzyme film is immobilized in hydrophilic polyurethane by the direct immobilization with an ammonium ion-selective membrane serving as a signal transducer, wire type and planar type electrodes are prepared. Responses toward urea for the wire type and planar type solid-state biosensors are observed. Regardless of the type of the base solid-state transducer employed, a similar response tendency is exhibited. In addition, the solid-state urea sensor fabricated by the direct immobilization retained 80% or greater of its initial urea response for two months, indicating the life span of the solid-state biosensor is similar to those of the urea sensors fabricated by the conventional crosslinking method.

The direct immobilization of the present invention is also applied for the biosensor membrane employing adenosine deaminase, as a bio-active reagent, which catalyzes the hydrolysis of adenosine to produce inosine and ammonium ions. In this case, a film of adenosine deaminase mixed with hydrophilic polyurethane is coated over ammonium-sensing wire type solid-state electrodes. An examination is made of the effect of the film thickness on the biosensor performance. The thinner the enzyme film is, the faster a response is detected. From this observation, it is recognized that the mass transfer of species between the external solution and the ion-selective surface is greatly affected by the thickness of the enzyme film.

In accordance with another embodiment of the present invention, the direct immobilization is applied for a glucose-sensing biosensor which employs glucose oxidase as a bio-active reagent. In this embodiment, polylysine is used at a small amount when mixing glucose oxidase with hydrophilic polyurethane, in order to enhance the permeability of the resulting hydrophilic polyurethane film. The signal transducer of this biosensor is a wire type solid-state electrode membrane which is of proton selectivity. The glucose oxidase catalyzes the oxidation of glucose to gluconic acid and the resulting pH is detected to quantitate the glucose. A slow response behavior to glucose is observed for the glucose sensor when a weakly buffered background electrolyte solution is used as usual. The reason is that the diffusion of glucose through the glucose oxidase immobilized hydrophilic polyurethane film is slow and a certain amount of time is required for the pH change of the buffer within the layer adjacent to the pH-sensing surface.

A better understanding of the present invention may be obtained in light of the following examples which are set forth to illustrate, but are not to be construed to limit the present invention.

EXAMPLE I

Preparation of Solid-State Type Biosensors

In an organic solvent was dissolved hydrophilic polyurethane which was then mixed with a bio-active reagent. The resulting solution was coated over an electrode membrane to form an enzyme film. Where the bio-active reagent was urease or adenosine deaminase, an organic solvent mixed with THF or methanol was used to dissolve the hydrophilic polyurethane. For glucose oxidase, the enzyme film was formed with a solution of hydrophilic polyurethane in THF. The reason why only THF was used for glucose oxidase was that it was found that glucose oxidase was deactivated in a mixed organic solvent of THF and methanol, but retained its catalytic activity when being immobilized by using THF.

1) Fabrication of Urea Sensors and Influence of Kinds of PU on Urea Sensor Performance Three biosensors for urea, which took advantage of the catalytic action of urease to hydrolyze urea into carbon dioxide and ammonia, were fabricated by mixing the enzyme with three polyurethane species different in the mole ratio of PPE to PPG and coating the mixtures over the electrode membranes. The compositions for the polyurethanes used are given in Table 1, below. Water uptake experiments showed a water uptake of 42 wt % for the hydrophilic polyurethane A, 100 wt % for the hydrophilic polyurethane B and 206 wt % for the hydrophilic polyurethane C.

TABLE 1

Compositions of Hydrophilic Polyurethane

| Compositions | HPU-A | HPU-B | HPU-C |
|---|---|---|---|
| PEG | 0.005 mol | 0.01 mol | 0.015 mol |
| PPG | 0.015 mol | 0.01 mol | 0.005 mol |
| Desmodur W[a] | 0.52 mol | 0.052 mol | 0.52 mol |
| Ethylene Glycol | 0.03 mol | 0.03 mol | 0.03 mol |
| PEG:PPG | 1:3 | 1:1 | 3:1 |

[a]Methylene bis(4-cyclohexyl isocyanate)

Figure 2A:
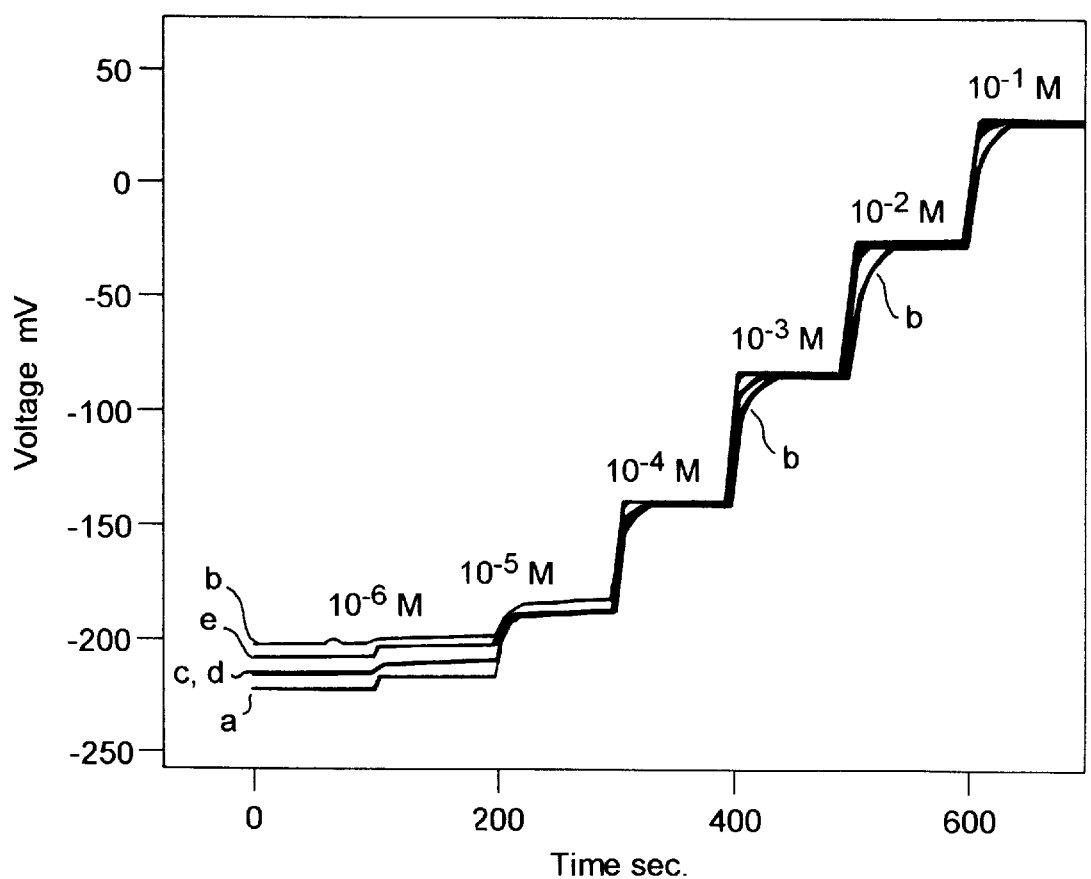
FIGS. 2a and 2b show the dynamic responses toward ammonium (2a) and urea (2b) for electrodes employing (a) an enzyme-lacking ammonium-selective polyurethane membrane, (b) a hydrophilic polyurethane A membrane on which a crosslinked urease film by gluataraldehyde is coated, (c) a hydrophilic polyurethane A membrane on which a urease film is directly immobilized, (d) a hydrophilic polyurethane B membrane on which a urease film is directly immobilized, and (e) a hydrophilic polyurethane C membrane on which a urease film is directly immobilized.
Figure 2B:
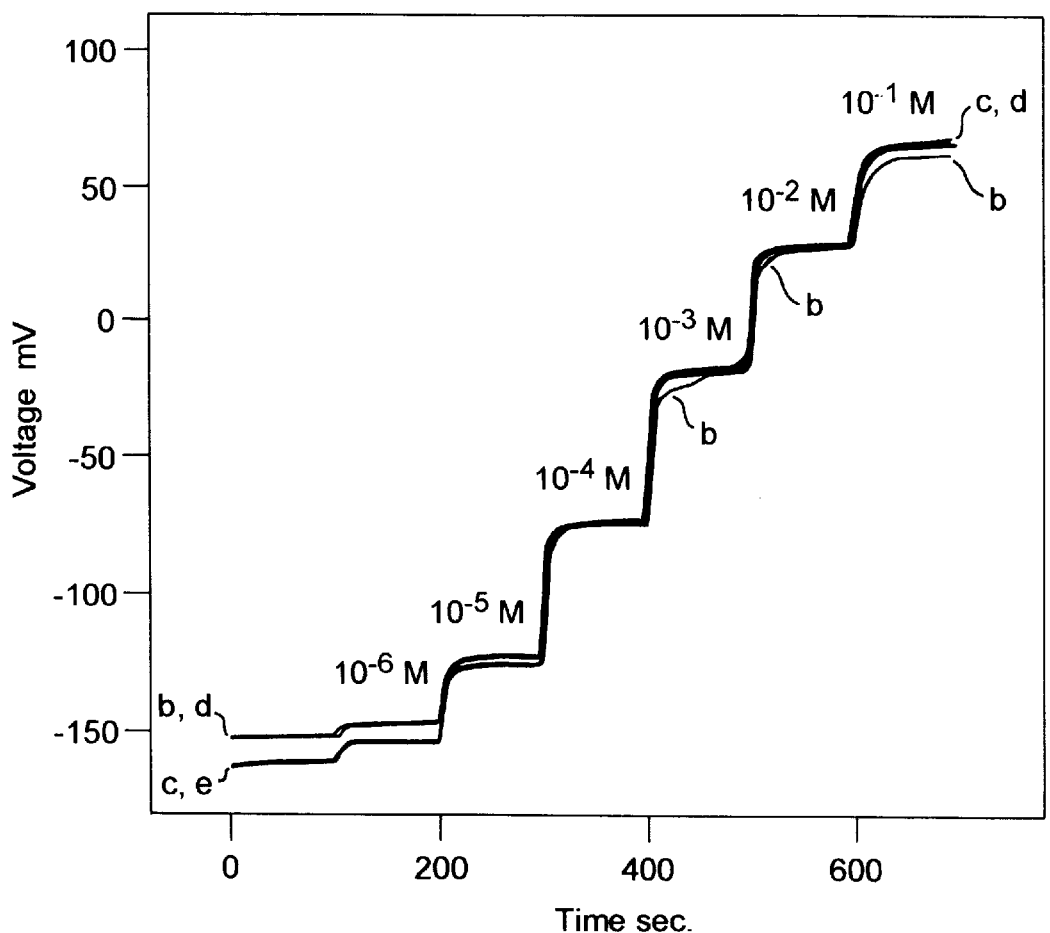

FIG. 2 illustrates dynamic responses observed toward ammonium (2a) and urea (2b) for urea sensors fabricated by use of conventional type electrodes. In the figures, the curve a was observed with an enzyme film-lacking ammonium selective membrane, the curve b with an asymmetric electrode membrane in which there is introduced an enzyme film crosslinked by glutaraldehyde, the curve c with an asymmetric electrode membrane in which there is introduced a polyurethane A film directly immobilized with urease, the curve d with an asymmetric electrode membrane in which there is introduced a polyurethane B film directly immobilized with urease, and the curve e with an asymmetric electrode membrane in which there is introduced a polyurethane C film directly immobilized with urease. As shown in FIG. 2a, the response capability and detection limit toward ammonium ion of the asymmetric membranes in which there were the hydrophilic polyurethane films directly immobilized with urease, were similar to those of the enzyme film lacking membrane. These data demonstrate that the presence of an additional hydrophilic polyurethane film does not significantly alter the intrinsic potentiometric response property of the underlying ammonium-sensing polymeric membrane. Because of having an enzyme film which consists of three layers of hydrophilic polyurethane, polylysine and enzyme, the asymmetric electrode membrane fabricated by the crosslinking method using glutaraldehyde is relatively slower in the response time to ammonium ions than is the electrode membrane which has an polyurethane film in which enzyme is directly immobilized. For a similar reason, the response toward urea was slower with the crosslinked urease membrane than with the membrane employing urease mixed with the three kinds of hydrophilic polyurethane. From the above data, it is apparent that all of the three membranes exhibit virtually the same response performance irrespective of the type of the hydrophilic polyurethane employed, indicating that their physical properties, i.e., water uptake properties do not affect the detection capabilities of the biosensors.

2) Fabrication of Urea Sensor and Influence of Kinds of Electrode on Urea Sensor Performance Urea sensors employing two different types of solid-state electrodes, i.e., wire type and planar type, were fabricated according to the above mentioned process and an examination was made of the response change according to the electrode types.

Figure 3:
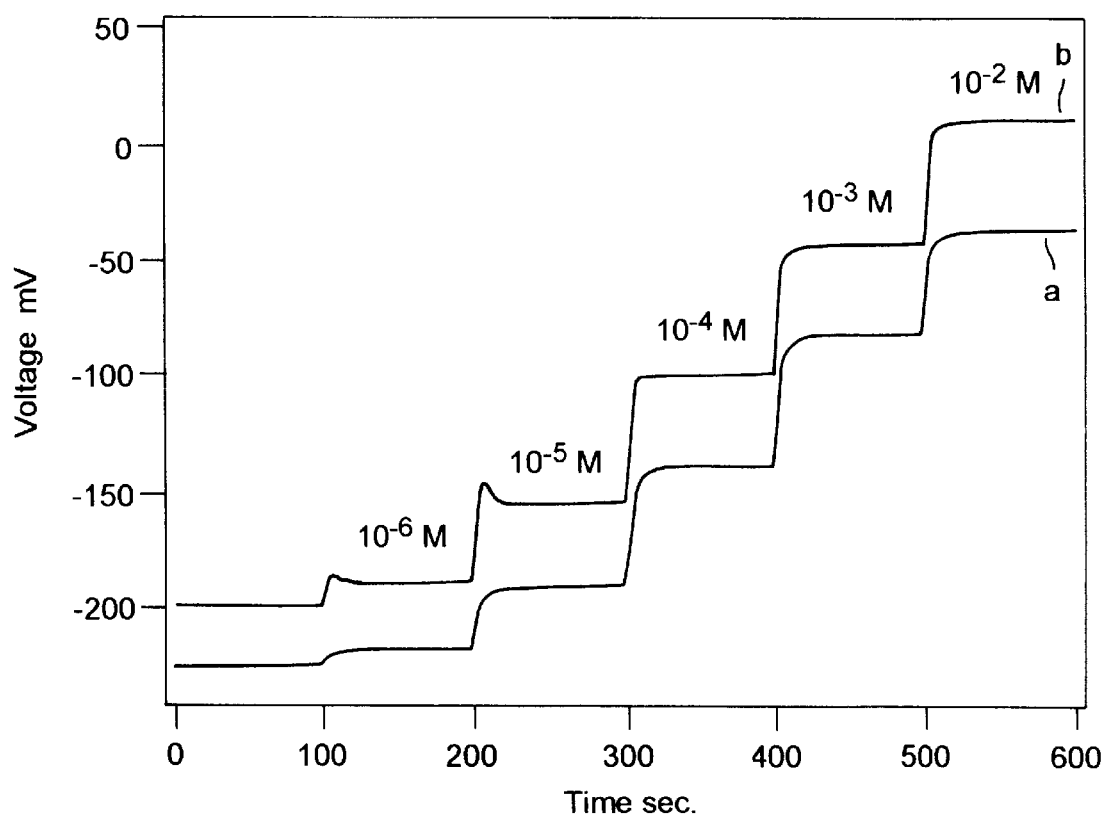
FIG. 3 shows the dynamic responses toward urea for the wire type (3a) and planar type (b0 biosensors employing the hydrophilic polyurethane asymmetric membrane in which a urease film is directly immobilized with an ammonium ion-selective film serving as a signal transducer.

FIG. 3 illustrates the dynamic responses observed toward urea for the wire type (curve a) and planar type (curve b) solid-state biosensors in which there were introduced the asymmetric hydrophilic polyurethane films directly immobilized with urease with ammonium ion-selective membranes serving as signal transducers. As seen in FIG. 3, regardless of the type of the base solid-state electrodes employed, a similar response behavior toward urea was observed for the biosensors with a slope of 52 mV/decade for the wire type and 55 mV/decade for the planar type in the range of $10^{-5}$–$10^{-2}$ M of urea. These values were essentially the same as those of the conventional type biosensors. In addition, the life span of the solid-state biosensor was similar to those of the conventional type biosensors. It was measured that the solid-state biosensor retained 80% or greater of its initial urea response for a two month period of time.

3) Fabrication of Adenosine Sensors and Influence of the Thickness of Enzyme Layers on Adenosine Sensor Performance The asymmetric polyurethane membrane system was applied for adenosine deaminase which catalyzes the hydrolysis of adenosine to produce inosine and ammonium ions. The biosensors thus fabricated were examined for the response change to inosine and ammonium ions according to the thickness of the enzyme film.

Figure 4A:
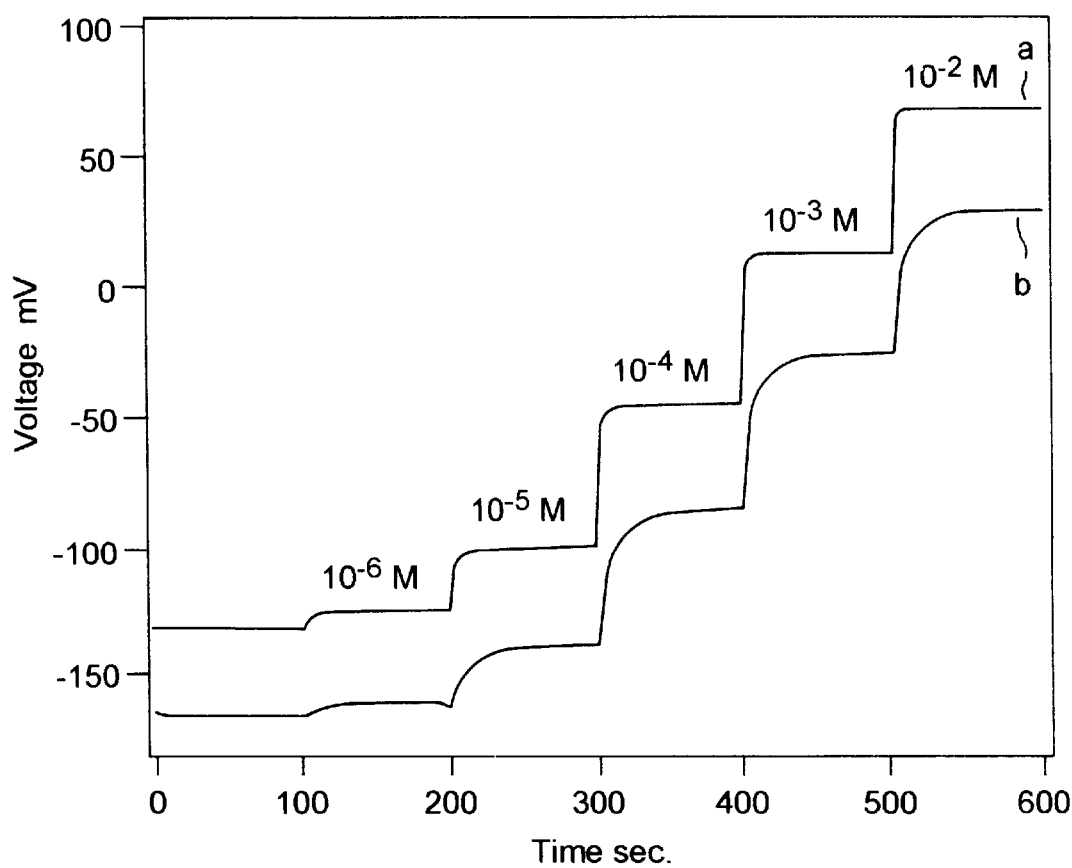
FIGS. 4a and 4b show the dynamic responses toward ammonium (4a) and adenosine (b) for wire type biosensors with (a) thin and (b) thick hydrophilic films directly immobilized with adenosine deaminase.
Figure 4B:
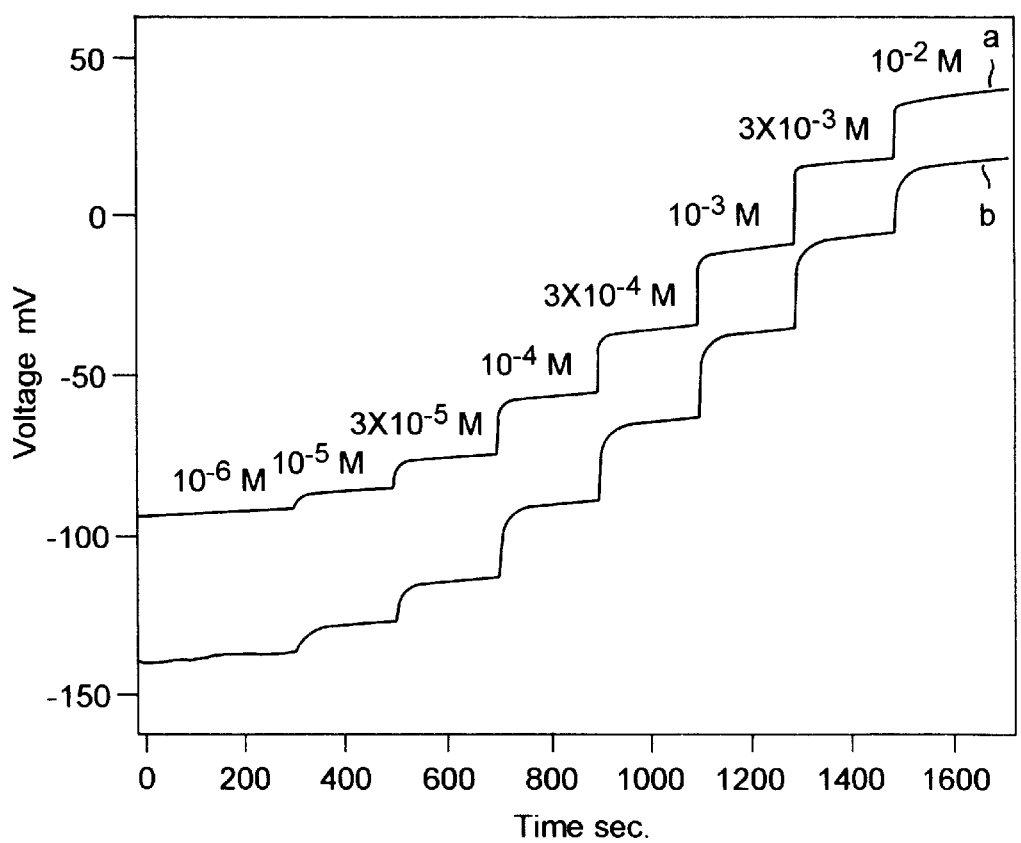

FIG. 4 illustrates the dynamic responses toward ammonium (4a) and adenosine (4b) for wire type solid-state biosensors in which there were introduced the hydrophilic polyurethane films directly immobilized with adenosine deaminase. In the figure, the curves a and b were obtained with a thick enzyme layer and a thin enzyme layer, respectively. As apparent from the curves, a faster response was observed toward both ammonium and adenosine for the sensor with the thinner enzyme layer by virtue of a fast mass transfer of species between the external bulk solution and the ion-selective surface. As for the potentiometric response to adenosine, however, a greater magnitude was obtained with the thicker biosensor as recognized from the data in which a response slope of 54 mV/decade for the thicker biosensor (curve a) and 46 mV/decade for the thinner biosensor (curve b) were obtained in the range of $10^{-5}$–$10^{-2}$ M of urea.

4) Fabrication and Performance of Glucose Sensor

Figure 5:
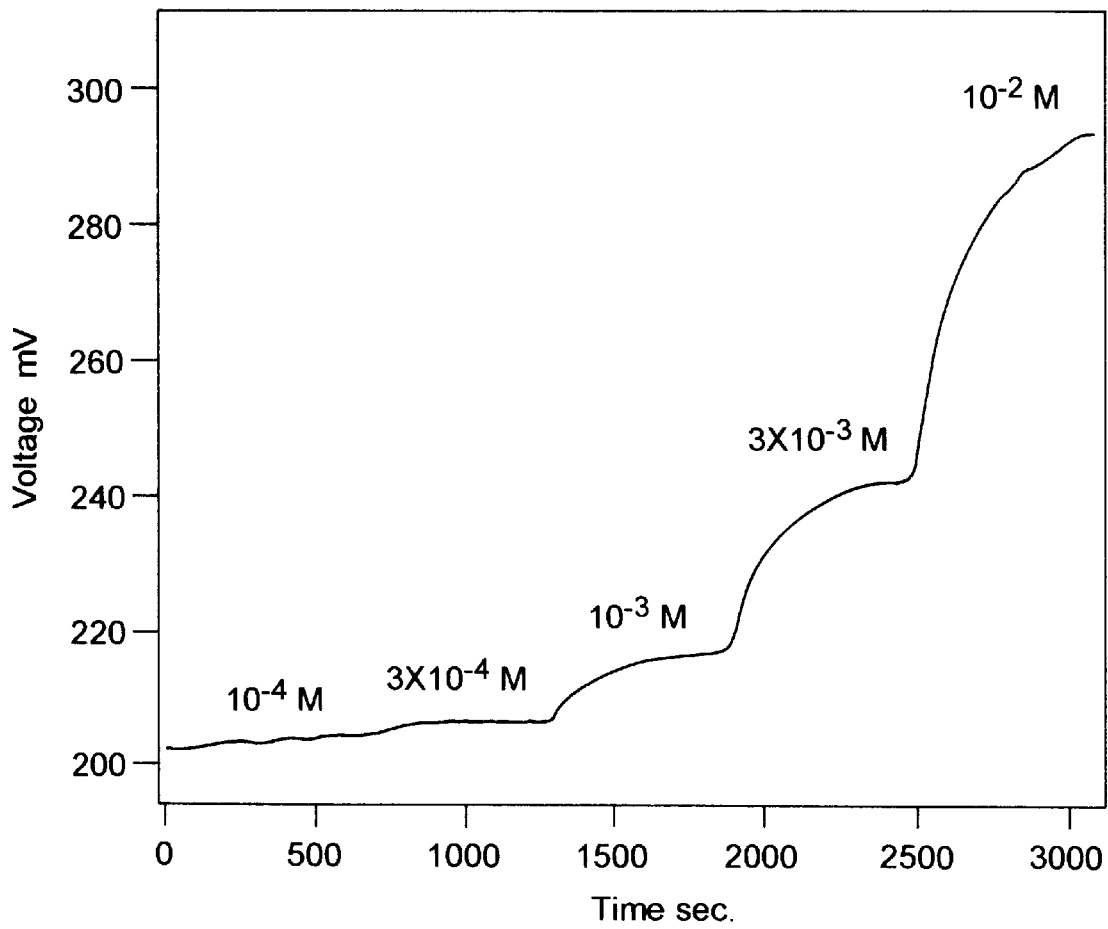
FIG. 5 shows the dynamic responses toward glucose in a buffered solution for a wire type biosensor based on the proton-selective asymmetric membrane coated with a hydrophilic polyurethane film directly immobilized with glucose oxidase.

Glucose biosensors were fabricated, which took advantage of the catalytic action of glucose oxidase, with proton-sensing wire type solid-state electrodes. A small amount of polylysine was added when directly immobilizing glucose oxidase in hydrophilic polyurethane membrane, with the aim of enhancing the permeability of the resulting polyurethane membrane. A response experiment was conducted in a weakly buffered background electrolyte solution. The glucose oxidase catalyzed the oxidation of glucose to gluconic acid while the signal transducers detected the resulting pH change. A response curve to glucose was obtained and is shown in FIG. 5. As seen, a slow response behavior was observed with the resulting glucose sensor, which may be attributed to a slow diffusion of glucose through the polyurethane membrane and to a certain amount of time required for the pH change of the buffer within the layer adjacent to the pH-sensing surface.

As described hereinbefore, the method using hydrophilic polyurethane, in accordance with the present invention, allows the simplification of the fabrication of biosensors without conducting complicated chemical reactions and washing steps, such as crosslinking. The enzyme entrapped within the hydrophilic polyurethane film can retain its high activity for an extended period of time and the intrinsic potentiometric response of the underlying ion-selective polymeric membrane is not affected by the enzyme immobilized polyurethane film coated on its sensing surface. Therefore, the biosensors fabricated according to the present invention are superior in specificity, selectivity, and stability. Further, the adoption of solid-state type electrodes by virtue of the direct immobilization of the bio-active reagents allows the biosensors to be miniaturized, offering the advantages of the detection of small quantities of samples and mass production for low cost.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for fabricating a biosensor composed of a signal detector and a signal transducer, comprising:
   a) obtaining a mixture solution by dissolving a mixture consisting essentially of hydrophilic polyurethane synthesized from polyethylene glycol, polypropylene glycol, ethylene glycol and diisocyanate, and a bioactive reagent into a solvent selected from the group consisting of tetrahydrofuran, methanol and mixture thereof; and b) directly immobilizing the mixture on the signal transducer by coating the mixture solution onto the signal transducer and then drying to form a membrane of the hydrophilic polyurethane having the bio-active reagent incorporated therein, wherein the hydrophilic polyurethane stabilizes the bio-active reagent and the bio-active reagent retains activity.

2. The method as set forth in claim 1, wherein the step of obtaining a mixture solution further includes dissolving polylysine in the solvent.

3. The method as set forth in claim 1, wherein the bio-active reagent is an enzyme.

4. The method as set forth in claim 1, wherein the polyethylene glycol and polypropylene glycol are used in a molar ratio range of from 1:10 to 10:1.

5. The method as set forth in claim 1, wherein the signal transducer utilizes potentiometry, voltametry or conductometry.

6. The method as set forth in claim 1, wherein the signal transducer is formed of at least one selected from the group consisting of silicon rubber, polyvinyl chloride and its derivatives, aromatic polyurethane and aliphatic polyurethane.

7. The method as set forth in claim 1, wherein the biosensor further comprises one of a conventional electrode and a solid electrode.

8. The method as set forth in claim 3, wherein the enzyme is selected from the group consisting of urease, adenosine deaminase and glucose oxidase.

9. The method as set forth in claim 2, wherein the bio-active reagent is an enzyme.

10. The method as set forth in claim 2, wherein the polyethylene glycol and polypropylene glycol are used in a molar ratio range of from 1:10 to 10:1.

11. The method as set forth in claim 2, wherein the signal transducer utilizes potentiometry, voltametry or conductometry.

12. The method as set forth in claim 2, wherein the signal transducer is formed of at least one selected from the group consisting of silicone rubber, polyvinyl chloride and its derivatives, aromatic polyurethane and aliphatic polyurethane.

13. The method as set forth in claim 2, wherein the biosensor further comprises one of a conventional electrode and a solid electrode.

14. The method as set forth in claim 9, wherein the enzyme is selected from the group consisting of urease, adenosine deaminase and glucose oxidase.

* * * * *